United States Patent [19]

Backstrom et al.

[11] Patent Number: 5,151,420
[45] Date of Patent: Sep. 29, 1992

[54] SUBSTITUTED PYRIDAZINONES

[75] Inventors: Reijo J. Backstrom, Helsinki; Kalevi E. Heinola, Jarvenpaa; Pentti T. Nore, Helsinki; Jarmo J. Pystynen, Espoo; Erkki J. Honkanen, Vantaa; Heimo O. Haikala, Espoo, all of Finland

[73] Assignee: Orion Corporation/Orion Pharmaceutica, Espoo, Finland

[21] Appl. No.: 489,187

[22] Filed: Mar. 8, 1990

Related U.S. Application Data

[63] Continuation of Ser. No. 404,532, Sep. 8, 1989, abandoned.

[30] Foreign Application Priority Data

Oct. 19, 1988 [GB] United Kingdom ............. 8824458

[51] Int. Cl.⁵ .......................................... C07D 237/14
[52] U.S. Cl. .................... 514/247; 514/252; 514/253
[58] Field of Search ................. 514/247; 544/239

[56] References Cited

U.S. PATENT DOCUMENTS

| | | | |
|---|---|---|---|
| 4,289,774 | 9/1981 | Schact et al. | 544/239 |
| 4,521,415 | 6/1985 | Katakami | 514/247 |
| 4,946,849 | 8/1990 | Coates et al. | 514/247 |
| 4,954,501 | 9/1990 | Herter | 544/239 |
| 5,019,575 | 5/1991 | Hakala et al. | 514/247 |

FOREIGN PATENT DOCUMENTS

| | | | |
|---|---|---|---|
| 57-46966 | 3/1982 | Japan | 544/239 |
| 60-857283 | 5/1985 | Japan | 544/238 |
| 87/03201 | 6/1987 | PCT Int'l Appl. | |
| 83-01447 | 4/1983 | World Int. Prop. O. | 514/247 |

OTHER PUBLICATIONS

H. Okushima et al., *J. Med. Chem.* 30(7), 1157-61 (1987), "A Novel Class of Cardiotonics...".
*Chemical Abstracts,* vol. 97, p. 653, No. 55827h, 1982.
*Chemical Abstracts,* vol. 103, p. 142000, No. 141996m, 1985.

*Primary Examiner*—Donald G. Daus
*Attorney, Agent, or Firm*—Wegner, Cantor, Mueller & Player

[57] ABSTRACT

Substituted benzylideneiminophyenylpyridazinones or dihydropyridazinones of formula I

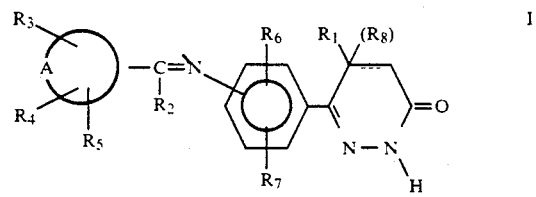

in which $R_1$ and $R_8$ independently mean hydrogen or lower alkyl, R2 is hydrogen, lower alkyl, trifluoromethyl, hydroxy alkyl, halogen alkyl, alkoxy alkyl, pyridyl, furyl, thienyl or cycloalkyl or one of optionally substituted groups; aryl, aralkyl, aralkenyl or nitrogen containing heterocyclic ring joining through an alkyl or alkenyl group and $R_3$, $R_4$ and $R_5$ independently mean hydrogen, lower alkyl, hydroxy alkyl, halogen, hydroxy, alkoxy, acyloxy, aroyloxy, formyl, acyl, cyano, amino, carboxy or trifluoromethyl, $R_6$ and $R_7$ independently mean hydrogen, amino, lower alkyl, hydroxy, nitro or cyano or $R_2$ and $R_7$ together form a —CH$_2$—NH— or —CH=N— group and A means phenyl, naphtyl or a nitrogen containing heterocyclic ring. The compounds may be used in the treatment of congestive heart failure.

22 Claims, No Drawings

SUBSTITUTED PYRIDAZINONES

This is a continuation application of U.S. application Ser. No. 07/404,532, filed Sep. 8, 1989, now abandoned.

The present invention relates to new substituted pyridazinones or dihydropyridazinones and salts thereof. The invention also relates to compositions containing these compounds and to a process for the preparation of the same.

The present compounds are useful as cardiotonic agents, antihypertensive agents and vasodilators for the treatment of congestive heart failure. The compounds are new.

The new compounds according to the present invention are substituted benzylideneiminophenylpyridazinones or dihydropyridazinones of formula I

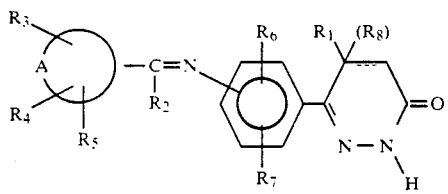

in which $R_1$ and $R_8$ independently mean hydrogen or lower alkyl. $R_2$ is hydrogen, lower alkyl, trifluoromethyl, hydroxy alkyl, halogen alkyl, alkoxy alkyl, pyridyl, furyl, thienyl or cycloalkyl or one of optionally substituted groups; aryl, aralkyl aralkenyl or nitrogen containing heterocyclic ring joining through an alkyl or alkenyl group and $R_3$, $R_4$ and $R_5$ independently mean hydrogen, lower alkyl, hydroxy alkyl, halogen, hydroxy, alkoxy, acyloxy, aroyloxy, formyl, acyl, cyano, amino, carboxy or trifluoromethyl, $R_6$ and $R_7$ independently mean hydrogen, amino, lower alkyl, hydroxy, nitro or cyano or $R_2$ and $R_7$ together form a —CH$_2$—NH— or —CH=N— group and A means phenyl, naphtyl or a nitrogen containing heterocyclic group.

The compounds according to formula I may be prepared in accordance with the following reaction sequences.

The substituted aminophenylpyridazinone or substituted aminophenyldihydropyridazinone moiety II

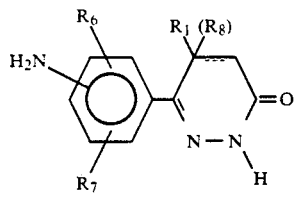

wherein $R_1$, $R_6$, $R_7$ and $R_8$ are the same as defined before, can be prepared according to the methods knowns in the literature.

Compound II is reacted with compound having formula III

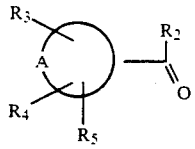

wherein $R_2$, $R_3$, $R_4$ and $R_5$ are the same as defined before, in neutral, acidic or basic conditions and in the absence or presence of an inert solvent at elevated temperatures to give compounds according to formula I in accordance with the present invention. Water from the reaction may be removed either by azeotropic destillation or by agents reacting or combining with water. Examples of these agents are metal oxides, anhydrous sodium sulphate, calcium sulphate or chloride etc.

Compounds III are either commercially available or the same are prepared by Friedel-Crafts reaction from compounds IV

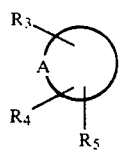

in which $R_3$, $R_4$, $R_5$ and A are the same as before and compounds V

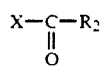

in which $R_2$ is as defined before and X is hydroxyl, halogen or other activated carboxylic acid derivative, in the presence of a suitable Friedel-Crafts catalyst.

The term "alkyl" as employed herein by itself or as part of another group includes both straight and branched chain radicals of up to 18 carbon atoms, preferably 1 to 8 carbon atoms, most preferably 1 to 4 carbon atoms. The term "lower alkyl" as employed herein by itself or as part of another group includes both straight and branched chain radicals of 1 to 7, preferably 1 to 4, most preferably 1 or 2 carbon atoms. Specific examples for the alkyl and lower alkyl residues, respectively, are methyl, ethyl, propyl, isopropyl, butyl, tert. butyl, pentyl, hexyl, octyl, decyl and dodecyl including the various branched chain isomers thereof.

The term "acyl" as employed herein by itself or as part of another group refers to an alkylcarbonyl or alkenylcarbonyl group, the alkyl and alkenyl groups being defined above.

The term "aroyl" as used herein by itself or as part of another group refers to an arylcarbonyl group, the aryl group being a monocyclic or bicyclic group containing from 6 to 10 carbon atoms in the ring portion. Specific examples for aryl groups are phenyl, naphtyl and the like.

The term "alkoxy" as employed herein by itself or as part of another group includes an alkyl residue as defined above linked to an oxygen atom.

The term "cycloalkyl" includes saturated cyclic hydrocarbon groups containing 3 to 8, preferably 5 to 7 carbon atoms. Specific examples are the cyclopentyl, cyclohexyl, cycloheptyl and adamantyl groups.

The term "aralkyl" as employed herein refers to alkyl groups as defined above having an aryl substituent. A specific example is the benzyl group and a phenyl-alkyl group having 2 to 3 carbon atoms in the alkyl moiety. In a correspobnding way "aralkenyl" means a group having a double bond in the alkyl moiety.

The term "halogen" as used herein refers to chlorine, bromine, fluorine or iodine, chlorine and bromine being preferred.

The term "nitrogen containing heterocyclic ring" as used herein refers to aromatic or non-aromatic rings having 1 to 3 nitrogen atoms in the ring. Specific examples are pyridyl, pyrrolyl, pyridazinyl, piperazinyl or triazinyl groups.

The term "optionally substituted" as used herein in connection with various residues refers to halogen substituents, such as fluorine, chlorine, bromine, iodine or trifluoromethyl groups, amino, alkyl, alkoxy, aryl, alkyl-aryl, halogen-aryl, cycloalkyl, alkylcycloalkyl, hydroxy, alkylamino, alkanoylamino, arylcarbonylamino, nitro, cyano, thiol, or alkylthio substituents.

The "optionally substituted" groups may contain 1 to 3, preferably 1 or 2, most preferably 1 of the above mentioned substituents.

The present compounds also form esters and the same also belong to the group of invented compounds. The esters readily hydrolyze in physiological circumstances and the same may be prepared by methods well known to chemists. Generally the first esters to hydrolyze in physiological circumstances are those attached to the hydroxyl groups in compounds according to Formula I. It is possible to esterify only one hydroxylic group or several of them if several hydroxylix groups are present. The ester forming groups are cleaved away in physiological circumstances and the active compounds are in this way liberated.

Salts of the compounds, when applicable, may be prepared by known methods. Physiologically acceptable salts are useful as active medicaments, however, preferred are the salts with hydrochloric, hydrobromic, phosphoric and sulfuric acids and with the organic acids like oxalic, fumaric, tartaric, malonic, acetic and citric acids etc.

The compounds according to this invention are formulated into dosage forms using the principles which are known to a person having average skills in the art. The compounds according to this invention are given to a patient as such or in combination with suitable pharmaceutical excipients in the form of tablets, dragees, capsules, suppositories, emulsions, suspensions or solutions whereby the contents of the active compound is in the formulation from about 1 to 100% per weight. Choosing suitable ingredients for the formulation is a routine for those of ordinary skill in the art. It is evident that suitable carriers, solvents, gel forming ingredients, dispersion forming ingredients, antioxidants, colours, sweeteners, wetting compounds and other ingredients normally used in this field of technology may be also used.

The compositions are given enterally or parenterally, the oral way being the easiest and preferred way.

The compositions are formulated depending upon the purpose of the medicine, normal uncoated tablets being quite satisfactory. Sometimes it is advisable to use coated tablets, i.e. so-called enterotablets, to secure that the medicine reaches the desired part of the gastrointestinal tract. Dragees and capsules may be used too. In a conventional way it is possible to make formulations which liberate the active ingredient slowly during a prolonged period of time.

It is also possible to give the desired dose of the medicine using suppositories. Suppositories are also given when the desired systemic effect is desired with patients having nausea and the like symptoms.

The present compounds may be given alone or in a combination with other medicines.

Congestive heart failure is characterized by the decrease in cardiac output and an increase in right and left ventricular filling pressure. These hemodynamic conditions can produce symptoms of dyspnea, fatigue and edema. Treatment of congestive heart failure usually focuses on the three principle factors determining cardiac performance: preload, impedance (afterload) and contractility. Vasodilation can improve cardiac function by reducing preload and/or afterload. Cardiac output can be increased directly by augmenting contractility.

The severity of congestive heart failure is usually classified by the New York Heart Association categories; Class I, II, III or IV. The therapeutic benefits of decreases in preload and afterload or in increases in contractility may vary among both classes and individual patients. Therefore, it may be advantageous to have compounds which produce varying degrees of vasodilation and increases in contractility. It is now described a series of compounds which, although similiar in structure, either increase in contractility alone or increase contractility with accompanying vasodilation.

Test Procedures

Male Wistar rats (320–380 g) were anesthetized with thiobarbital sodium (Inactin, Byk Gulden, Germany) by administration of 160 mg/kg intraperitoneally. In each rat, the trachea was cannulated with a polyethylene tube and the animal was allowed to breath spontaneously. The left femoral artery was cannulated with fluid-filled (0.9% saline+heparin) PE-50 tubing and connected to a pressure transducer (MP-15, Micron Instruments, California USA). Cannulation of the left ventricle was done via the right carotid artery using fluid-filled PE-50 tubing connected to a pressure transducer. The left femoral vein was cannulated for drug or vehicle injections. Rectal temperature was monitored and the rat body temperature was maintained at $38°\pm0.3°$ C. with a thermostatically-controlled heating pad. The outputs of the pressure transducers were amplified (HP-8805D, Hewlett-Packard, USA) and coupled to a PDP-11/23 computer (Digital Equipment Corp., USA), which acquired and analyzed the signals in real-time. At minute intervals, the heart rate (HR), mean arterial pressure (MAP) and the left ventricular pressure derivative (LV dP/dt) were calculated and printed-out. Each test compound was dissolved in 0.05 N NaOH and diluted with 0.9% saline to give a final concentration of 1 $\mu$mol/ml. After a stabilization period of 40 min, four doses (0.01, 0.03, 0.1 and 0.3 $\mu$mol) of the test compound were given in a 1 ml/kg bolus at 30 min intervals. Control rats received only vehicle. The results were expressed as mean $\pm$SE. Differences between the experimental and control groups were calculated using Students t-test for independent observations. A probability value of $p<0.05$ was considered significant.

Following compounds were tested according to the above described procedure:

Compound A:

Compound A:
6-[4-(2,4-Dihydroxyphenyl)methyleneaminophenyl]-4,5-dihydropyridazin-3(2H)one Compound B:
6-[4-(1-(2,4-Dihydroxyphenyl)ethylidene)aminophenyl]-4,5-dihydropyridazin-3(2H)one Compound C:
6-[4-(2,4-Dihydroxyphenyl)benzylidene)aminophenyl]-4,5-dihydropyridazin-3(2H)one Compound D:
6-[4-(1-(2,4-Dihydroxyphenyl)ethylidene)aminophenyl]-4,5-dihydro-5-methylpyridazin-3(2H)one Compound E:
6-[4-(1-(2,4-Dihydroxyphenyl)propylidene)aminophenyl]-4,5-dihydropyridazin-3(2H)one Compound F:
6-[4-(2-hydroxynaphtyl)methyleneaminophenyl]-4,5-dihydropyridazin-3(2H)one Compound G:
6-[4-(2-hydroxyphenyl)methyleneaminophenyl]-4,5-dihydropyridazin-3(2H)one Compound H:
6-[4-(1-(2,4-Dihydroxyphenyl)ethylidene)aminophenyl]pyridazin-3(2H)one Compound I:
6-[4-(1-(4-Pyridyl)ethylidene)aminophenyl]-4,5-dihydropyridazin-3(2H)one Compound L:
6-[4-(1-(2,4-dihydroxyphenyl)-3-phenylpropylidene)-aminophenyl]-4,5-dihydropyridazin-3(2H)one Compound M:
6-[4-(2,4-dihydroxyphenyl)benzylideneaminophenyl]-5-methyl-4,5-dihydropyridazin-3(2H)one Compound N:
6-[4-(2-hydroxyphenyl)methyleneaminophenyl]-5-methyl-4,5-dihydropyridazin-3(2H)one Compound O:
6-[4-(1-(2,4-dihydroxyphenyl)-2-(4-hydroxyphenyl)ethylidene)aminophenyl]-4,5-dihydropyridazin-3(2H)one Compound P:
6-[4-(1-(2,4-dihydroxyphenyl)-1-(3,4-dimethoxyphenyl)-methylene-aminophenyl]-4,5-dihydropyridazin-3(2H)one Compound R:
6-[4-(1-(2,4-dihydroxyphenyl)-3-(3,4-dimethoxyphenyl)propylidene-aminophenyl]-4,5-dihydropyridazin-3(2H)one Compound S:
6-[4-(1-(2,4-dihydroxyphenyl)-2-(3,4-dichlorophenyl)ethylidene-aminophenyl]-4,5-dihydropyridazin-3(2H)one Compound T:
6-[4-(1-(2,4-dihydroxyphenyl)-4-phenyl-butylidene)aminophenyl]-4,5-dihydropyridazin-3(2H)one Compound U:
6-[4-(1-(2,4-dihydroxyphenyl)-3,3-diphenyl)-propylidene)aminophenyl]-4,5-dihydropyridazin-3(2H)one The compounds used as reference in the tests have following chemical names:

Pimopendan:
4,5-Dihydro-6-(2-(4-methoxyphenyl)-1H-benzimidazol-5-yl)-5-methyl-3(2H)-pyridazinone MCI-154:
4,5-Dihydro-6-(4-(4-pyridinylamino)phenyl)-3(2H)-pyridazinone monohydrochloride BM 14.478:
5,7-Dihydro-7,7-dimethyl-2-(4-pyridinyl)-pyrrolo-(2,3-f)benzimidazol-6(1H)-one The results of the tests are shown in Tables 1–5. In Table 5 the concentration of the compounds showing 50% inhibition of Canine Cardiac Phosphodiesterase III enzyme is given.

TABLE 1

| | | 1st dose (0.01 μmol) | |
|---|---|---|---|
| Test Compound | n | Maximal Percent change | Duration of Action (>5%) |
| | | LV dP/dt | |
| A | 4 | 4 ± 1 | — |
| B | 9 | 11 ± 4 | 3 min |
| C | 7 | 5 ± 1 | 1 min |
| D | 9 | 7 ± 2 | 1 min |
| E | 7 | 4 ± 1 | — |
| F | | | |
| G | 10 | 3 ± 1 | — |
| H | 8 | 5 ± 1 | — |
| I | | | |
| L | 5 | 3 ± 1 | — |
| M | 7 | 14 ± 4 | >30 min |
| N | 7 | 10 ± 1 | 7 min |
| O | 6 | 1 ± 1 | — |
| P | 8 | 5 ± 1 | — |
| R | 6 | 4 ± 1 | — |
| S | 6 | 4 ± 2 | — |
| T | 2 | 2 ± 1 | — |
| U | 4 | 2 ± 2 | — |
| Pimobendan | 7 | 4 ± 2 | — |
| MCI-154 | 6 | 13 ± 5 | 5 min |
| BM 14.478 | 6 | 9 ± 1 | 12 min |
| | | MAP | |
| A | 5 | −1 ± 1 | — |
| B | 9 | 1 ± 1 | — |
| C | 7 | 2 ± 0.5 | — |
| D | 10 | −7 ± 1 | 1 min |
| E | 7 | −2 ± 1 | — |
| F | | | |
| G | 10 | −7 ± 1 | — |
| H | 9 | −7 ± 1 | 1 min |
| I | | | |
| L | 6 | −5 ± 2 | — |
| M | 7 | −10 ± 2 | >30 min |
| N | 8 | −6 ± 1 | — |
| O | 8 | −2 ± 1 | — |
| P | 9 | −6 ± 1 | — |
| R | 6 | −6 ± 2 | — |
| S | 7 | −9 ± 1 | — |
| T | 3 | 3 ± 4 | — |
| U | 5 | −6 ± 2 | — |
| Pimobendan | 6 | −1 ± 1 | — |
| MCI-154 | 6 | −3 ± 2 | — |
| BM 14.478 | 9 | −5 ± 1 | >30 min |
| | | HR | |
| A | 5 | 1 ± 1 | — |
| B | 9 | −1 ± 0.3 | — |
| C | 7 | 2 ± 0.3 | — |
| D | 10 | 3 ± 1 | — |
| E | 7 | 1 ± 0.4 | — |
| F | | | |
| G | 10 | 2 ± 1 | — |
| H | 9 | 1 ± 0.4 | — |
| I | | | |
| L | 6 | −3 ± 1 | — |
| M | 7 | −5 ± 1 | 1 min |
| N | 8 | −2 ± 0.3 | — |
| O | 8 | −2 ± 1 | — |
| P | 9 | −2 ± 0.3 | — |
| R | 6 | −2 ± 1 | — |
| S | 7 | −1 ± 0.4 | — |
| T | 3 | −1 ± 1 | — |
| U | 5 | −0.2 ± 0.5 | — |
| Pimobendan | 6 | −2 ± 1 | — |
| MCI-154 | 6 | 2 ± 1 | — |
| BM 14.478 | 9 | 3 ± 1 | — |

TABLE 2

| Test Compound | n | 2nd dose (0.03 μmol) Maximal Percent change | Duration of Action (>5%) |
|---|---|---|---|
| | | LV dP/dt | |
| A | 4 | 6 ± 2 | — |
| B | 9 | 16 ± 6 | >30 min |
| C | 6 | 8 ± 2 | 5 min |
| D | 9 | 13 ± 3 | >30 min |
| E | 7 | 8 ± 2 | 1 min |
| F | | | |
| G | 10 | 6 ± 1 | — |
| H | 8 | 5 ± 1 | — |
| I | | | |
| L | 6 | 11 ± 2 | — |
| M | 7 | 28 ± 7 | >30 min |
| N | 7 | 23 ± 5 | >30 min |
| O | 6 | 6 ± 1 | — |
| P | 8 | 9 ± 3 | — |
| R | 6 | 7 ± 1 | 3 min |
| S | 6 | 8 ± 2 | 2 min |
| T | 3 | 8 ± 3 | — |
| U | 4 | 6 ± 1 | — |
| Pimobendan | 7 | 8 ± 4 | 5 min |
| MCI-154 | 6 | 20 ± 4 | 8 min |
| BM 14.478 | 6 | 16 ± 3 | >30 min |
| | | MAP | |
| A | 5 | −2 ± 1 | — |
| B | 9 | 2 ± 1 | — |
| C | 7 | 1 ± 1 | — |
| D | 10 | −13 ± 1 | >30 min |
| E | 7 | −2 ± 0.2 | — |
| F | | | |
| G | 10 | −6 ± 1 | — |
| H | 9 | −7 ± 1 | — |
| I | | | |
| L | 6 | −7 ± 2 | — |
| M | 7 | −19 ± 2 | >30 min |
| N | 8 | −10 ± 1 | 12 min |
| O | 8 | −2 ± 1 | — |
| P | 9 | −7 ± 3 | — |
| R | 6 | −5 ± 1 | — |
| S | 7 | −6 ± 2 | — |
| T | 3 | −1 ± 2 | — |
| U | 5 | −4 ± 7 | — |
| Pimobenden | 6 | −3 ± 1 | — |
| MCI-154 | 6 | −9 ± 3 | 1 min |
| BM 14.478 | 9 | −14 ± 2 | >30 min |
| | | HR | |
| A | 5 | 2 ± 1 | — |
| B | 9 | 1 ± 1 | — |
| C | 7 | 3 ± 1 | — |
| D | 10 | 5 ± 1 | 1 min |
| E | 7 | 2 ± 0.2 | — |
| F | | | |
| G | 10 | 3 ± 1 | — |
| H | 9 | 2 ± 0.2 | — |
| I | | | |
| L | 6 | 3 ± 0.4 | — |
| M | 7 | 9 ± 1 | >30 min |
| N | 8 | 6 ± 1 | 6 min |
| O | 8 | 2 ± 0.5 | — |
| P | 9 | 2 ± 0.3 | — |
| R | 6 | 2 ± 0.2 | — |
| S | 7 | 3 ± 0.5 | — |
| T | 3 | −1 ± 1 | — |
| U | 5 | 1 ± 1 | — |
| Pimobendan | 6 | −3 ± 4 | — |
| MCI-154 | 6 | 4 ± 1 | — |
| BM 14.478 | 9 | 5 ± 1 | 9 min |

TABLE 3

| Test Compound | n | 3rd dose (0.1 μmol) Maximal Percent change | Duration of Action (>5%) |
|---|---|---|---|
| | | LV dP/dt | |
| A | 4 | 12 ± 4 | 14 min |
| B | 9 | 17 ± 8 | >30 min |
| C | 6 | 12 ± 4 | 15 min |
| D | 9 | 18 ± 5 | >30 min |
| E | 7 | 12 ± 3 | >30 min |
| F | | | |
| G | 10 | 9 ± 1 | 4 min |
| H | 8 | 9 ± 2 | 6 min |
| I | | | |
| L | 6 | 27 ± 3 | 8 min |
| M | 7 | 39 ± 10 | >30 min |
| N | 7 | 41 ± 10 | >30 min |
| O | 6 | 5 ± 1 | — |
| P | 8 | 12 ± 1 | 4 min |
| R | 6 | 9 ± 1 | 5 min |
| S | 6 | 10 ± 2 | 7 min |
| T | 3 | 10 ± 2 | 2–11 min |
| U | 4 | 7 ± 4 | — |
| Pimobendan | 7 | 13 ± 2 | 10 min |
| MCI-154 | 6 | 23 ± 4 | 22 min |
| BM 14.478 | 6 | 31 ± 4 | >30 min |
| | | MAP | |
| A | 5 | −4 ± 1 | — |
| B | 9 | −6 ± 1 | 1 min |
| C | 7 | −7 ± 2 | 1 min |
| D | 10 | −21 ± 2 | >30 min |
| E | 7 | −9 ± 3 | 1 min |
| F | | | |
| G | 10 | −11 ± 2 | 2 min |
| H | 9 | −7 ± 1 | 1 min |
| I | | | |
| L | 6 | −10 ± 3 | 1 min |
| M | 7 | −28 ± 3 | >30 min |
| N | 8 | −12 ± 2 | >30 min |
| O | 8 | −2 ± 1 | — |
| P | 9 | −6 ± 2 | — |
| R | 6 | −7 ± 1 | — |
| S | 7 | −6 ± 1 | — |
| T | 3 | −3 ± 3 | — |
| U | 5 | −2 ± 2 | — |
| Pimobendan | 6 | −1 ± 4 | — |
| MCI-154 | 6 | −25 ± 4 | >30 min |
| BM 14.478 | 9 | −28 ± 3 | >30 min |
| | | HR | |
| A | 5 | 3 ± 1 | — |
| B | 9 | 3 ± 0.3 | — |
| C | 7 | 5 ± 1 | 1 min |
| D | 10 | 10 ± 1 | >30 min |
| E | 7 | 2 ± 0.2 | — |
| F | | | |
| G | 10 | 3 ± 0.4 | — |
| H | 9 | 3 ± 0.3 | — |
| I | | | |
| L | 6 | 6 ± 2 | 1 min |
| M | 7 | 10 ± 1 | >30 min |
| N | 8 | 10 ± 1 | >30 min |
| O | 8 | 2 ± 0.5 | — |
| P | 9 | 3 ± 0.4 | — |
| R | 6 | 3 ± 1 | — |
| S | 7 | 3 ± 1 | — |
| T | 3 | 1 ± 1 | — |
| U | 5 | 2 ± 1 | — |
| Pimobendan | 6 | −4 ± 4 | — |
| MCI-154 | 6 | 6 ± 1 | 8 min |
| BM 14.478 | 9 | 11 ± 1 | >30 min |

TABLE 4

| Test Compound | n | 4th dose (0.3 μmol) Maximal Percent change | Duration of Action (>5%) |
|---|---|---|---|
| A | 4 | 12 ± 1 | 10 min |
| B | 9 | 28 ± 11 | >30 min |
| C | 6 | 17 ± 7 | >30 min |
| D | 9 | 29 ± 10 | >120 min |
| E | 7 | 19 ± 4 | >30 min |
| F | | | |
| G | 10 | 14 ± 2 | 10 min |
| H | 8 | 10 ± 3 | 6 min |

TABLE 4-continued

| | 4th dose (0.3 μmol) | | |
|---|---|---|---|
| Test Compound | n | Maximal Percent change | Duration of Action (>5%) |
| I | | | |
| L | 6 | 32 ± 5 | 14 min |
| M | 7 | 42 ± 12 | >30 min |
| N | 7 | 42 ± 12 | >30 min |
| O | 6 | 11 ± 3 | 4 min |
| P | 8 | 22 ± 5 | 24 min |
| R | 6 | 14 ± 9 | 7 min |
| S | 6 | 14 ± 4 | 13 min |
| T | 3 | 14 ± 2 | 4->30 min |
| U | 4 | 14 ± 4 | 8 min |
| Pimobendan | 7 | 21 ± 4 | >30 min |
| MCI-154 | 6 | 31 ± 13 | >30 min |
| BM 14.478 | 6 | 35 ± 5 | >30 min |
| MAP | | | |
| A | 5 | −15 ± 4 | >30 min |
| B | 9 | −14 ± 3 | 2 min |
| C | 7 | −12 ± 3 | >30 min |
| D | 7 | −34 ± 3 | >120 min |
| E | 7 | −13 ± 3 | 2 min |
| F | | | |
| G | 10 | −15 ± 4 | 2 min |
| H | 9 | −16 ± 3 | 16 min |
| I | | | |
| L | 6 | −21 ± 3 | 1 min |
| M | 7 | −37 ± 4 | >30 min |
| N | 8 | −24 ± 2 | >30 min |
| O | 8 | −1 ± 1 | — |
| P | 9 | −14 ± 4 | 2 min |
| R | 6 | −20 ± 2 | >30 min |
| S | 7 | −19 ± 5 | >30 min |
| T | 3 | 1 ± 5 | — |
| U | 5 | 0.4 ± 4 | — |
| Pimobendan | 6 | −14 ± 7 | 1 min |
| MCI-154 | 6 | −31 ± 3 | >30 min |
| BM 14.478 | 9 | −40 ± 3 | >30 min |
| HR | | | |
| A | 5 | 4 ± 1 | — |
| B | 9 | 5 ± 1 | 1 min |
| C | 7 | 8 ± 1 | >30 min |
| D | 7 | 11 ± 1 | >120 min |
| E | 7 | 3 ± 0.3 | — |
| F | | | |
| G | 10 | 5 ± 1 | 2 min |
| H | 9 | 6 ± 1 | 1 min |
| I | | | |
| L | 6 | 7 ± 1 | 1 min |
| M | 7 | 11 ± 1 | >30 min |
| N | 8 | 12 ± 1 | >30 min |
| O | 8 | 3 ± 0.3 | — |
| P | 9 | 5 ± 0.3 | — |
| R | 6 | 4 ± 1 | — |
| S | 7 | 4 ± 1 | — |
| T | 3 | 2 ± 1 | — |
| U | 5 | 2 ± 2 | — |
| Pimobendan | 6 | 0 ± 2 | — |
| MCI-154 | 6 | 7 ± 2 | 11 min |
| BM 14.478 | 9 | 14 ± 2 | >30 min |

TABLE 5

| Canine Cardiac Phosphodiesterase III | |
|---|---|
| Compound | IC$_{50}$ (μM) |
| A | 1.7 |
| B | 0.19, 0.05 |
| C | 0.019 |
| D | 0.06, 0.1 |
| E | 0.39 |
| F | >10.0 |
| G | |
| H | 0.14 |
| I | |
| L | 0.002 |
| M | 0.11, 0.003 |
| Pimobendan | 2.0, 1.5 |
| MCI-154 | 2.5, 0.37 |
| BM 14.479 | 0.94 |

The preparation of the compounds according to the invention are described in detail in following Examples.

EXAMPLE 1

6-[4-(2,4-Dihydroxyphenyl)methyleneaminophenyl]-4,5-dihydropyridazin-3(2H)one

A solution containing 0.42 g (0.003 mol) of 2,4-dihydroxybenzaldehyde, 0.57 g (0.003 mol) of 6-(4-aminophenyl)-4,5-dihydropyridazin-3(2H)one and 0.05 ml of acetic acid in a mixture of 40 ml of ethanol and 20 ml of DMF was refluxed for 4 h. After cooling the product was filtered and washed with ethanol. Yield 0.80 g (85%), m.p. 350° C. (decomp).

EXAMPLE 2

6-[4-(1-(2,4-Dihydroxyphenyl)ethylidene)aminophenyl]-4,5-dihydropyridazin-3(2H)one A mixture containing 0.91 g (0.006 mol) of 2',4'-dihydroxyacetophenone and 0.95 g (0.005 mol) of 6-(4-aminophenyl)-4,5-dihydropyridazin-3(2H)one was heated for 4 h at 140° C. in a stream of nitrogen gas. The product was triturated with boiling ethanol and filtered. Yield 0.88 g (54%), m.p. 350° C. (decomp).

EXAMPLE 3

6-[4-(2,4-Dihydroxyphenyl)benzylidene)aminophenyl]-4,5-dihydropyridazin-3(2H)one A mixture of 1.3 g (0.006 mol) 2,4-dihydroxybenzophenone and 0.95 g (0.005 mol) of 6-(4-aminophenyl)-4,5-dihydropyridazin-3(2H)one was heated for 3 h at 140° C. in a stream of nitrogen gas. The product was crystallized from ethanol. Yield 0.38 g (17%), m.p. 345°-350° C.

EXAMPLE 4

6-[2,4-Dimethyl-3-((2,4-dihydroxyphenyl)methylene)aminophenyl)]-4,5-dihydropyridazin-3(2H) one A mixture of 0.43 g (0.002 mol) of 6-(3-amino-2,4-dimethylphenyl)-4,5-dihydropyridazin-3(2H) one, 0.28 g (0.002 mol) of 2,4-dihydroxybenzaldehyde and few drops of DMA was heated for 1.5 h at 150° C. The product was triturated with acetone, filtered and washed with acetone. Yield 0.43 g (65 %), m.p. 280°-283° C.

EXAMPLE 5

6-[4-(1-(2,4-Dihydroxyphenyl)ethylidene)aminophenyl]-4,5-dihydro-5-methylpyridazin-3(2H)one A mixture of 0.167 g (0.0011 mol) of 2',4'-dihydroxypropiophenone and 0.203 g (0,001 mol) of 6-(4-aminophenyl)-4,5-dihydro-5-methylpyridazin-3(2H)one was heated for 1 h at 140° C. The product was triturated with ethanol and filtered. Yield 0.15 g (45%), m.p. 185°-190° C.

EXAMPLE 6

6-[4-(1-(2,4-dihydroxyphenyl)propylidene)aminophenyl]-4,5-dihydro-pyridazin-3(2H)one A solution containing 1.0 g (0.006 mol) of 2',4'-dihydroxypropiophenone and 0.57 g (0.003 mol) of 6-(4- aminophenyl)-4,5-dihydropyridazin-3(2H)one in 10 ml of DMA was heated for 20 h at 140° C. The solvent was evaporated in vacuo and the residue was crystallized from ethanol. Yield 0.05 g (5%), m.p. 350° C. (decomp).

EXAMPLE 7

6-[4-(1-(4-Pyridyl)ethylidene)aminophenyl]-4,5-dihydropyridazin-3(2H)one

A solution containing 0.36 g (0.003 mol) of 4-acetylpyridine and 0.57 g (0.003 mol) of 6-(4-aminophenyl)-4,5-dihydropyridazin-3(2H)one in a mixture of 40 ml of toluene and 40 ml of DMT was refluxed over night with a Dean-Stark separator in the presence of catalytic amount of conc. $H_2SO_4$. The solvents were evaporated in vacuo and the residue treated with $NaHCO_3$-solution. The product was filtered and crystallized from ethanol. Yield 0.53 g (60%).

EXAMPLE 8

6-[4-(1-(2,4-dihydroxyphenyl)-3-phenyl-propylidene)aminophenyl]-4,5-dihydropyridazin-3(2H)one A mixture containing 1.45 g of 1-(2,4-dihydroxyphenyl)3-phenyl-propan-1-one and 6-(4-aminophenyl)-4,5-dihydropyridazin-3(2H)one was heated for 72 h at 190° C. The product was treated with ethyl acetate, yield 0.37 g (16%), m.p. 208°-210° C.

EXAMPLE 9

6-[4-(4-hydroxyphenyl)methyleneaminophenyl]-4,5-dihydroxypyridazin-3(2H)one

A solution containing 0.61 g of 4-hydroxybenzaldehyde, 0.95 g of 6-(4-aminophenyl)-4,5-dihydropyridazin-3(2H)one, 1 ml of acetic acid and 10 ml of N,N-dimethylacetamide in 40 ml of ethanol was refluxed for 16 h. The product was filtered and washed with ethanol. yield 1.14 g (77%), m.p. 233° C.

EXAMPLE 10

6-[4-(4-trifluoromethylphenyl)methyleneaminophenyl]-4,5-dihydropyridazin-3(2H)one A solution containing 0.87 g of 4-trifluoromethylbenzaldehyde, 6-(4-aminophenyl-4,5-dihydropyridazin-3(2H)one, 1 ml of acetic acid and 10 ml of N,N-dimethylacetamide in 40 ml of ethanol was refluxed for 5 h. The product was filtered and washed with ethanol. Yield 0.7 g (41%), m.p. 245°-247° C.

EXAMPLE 11

6-[4-(2,4-dihydroxyphenyl)benzylideneaminophenyl]-5-methyl4,5-dihydropyridazin-3(2H)one A mixture containing 0.25 g of 2,4-dihydroxybenzophenone and 0.2 g of 6-(4-aminophenyl)-5-methyl-4,5-dihydropyridazin-3(2H)one was heated for 7 h at 142°-145° C. The product was crystallized from ethanol. Yield 0.15 g (38%), m.p 291°-297° C.

EXAMPLE 12

6-[4-(2-hydroxyphenyl)methyleneaminophenyl]-5-methyl-4,5-dihydropyridazin-3(2H)one A mixture containing 0.146 g of salicyl aldehyde and 6-(4-aminophenyl)-5-methyl-4,5-dihydropyridazin-3(2H)one was heated for 10 minutes at 140° C. The product was crystallized from ethyl acetate. Yield 0.2 g (65%), m.p. 207°-209° C.

EXAMPLE 13

6-[4-(1-(2,4-dihydroxyphenyl)-2-(4-hydroxyphenyl)ethylidene)-aminophenyl]-4,5-dihydropyridazin-3(2H)one A mixture containing 1.22 g of 1-(2,4-dihydroxyphenyl)-2-(4-hydroxyphenyl)ethan-1-one and 0.95 g of 6-(4-aminophenyl)-4,5-dihydro-pyridazin-3(2H)one was heated for 7.5 h at 180° C. The product was treated with ethyl acetate and crystallized from ethanol. Yield 0.74 g (54%), m.p. 296°-299° C.

EXAMPLE 14

6-[4-(1-(2,4,6-trihydroxyphenyl)ethylidene)aminophenyl]-4,5dihydropyridazin-3(2H)one A mixture containing 0.97 g 2', 4', 6'-trihydroxyacetophenone and 0.95 g of 6-(4-aminophenyl)-4,5-dihydropyridazin-3(2H)one was heated for 4 h at 160° C. The product was treated with ethanol. Yield 1.24 g, m.p. 300°-310° C.

EXAMPLE 15

6-[4-(1-(2-hydroxy-4-methoxyphenyl)ethylidene)aminophenyl]-4,5-dihydropyridazin-3(2H)one A mixture containing 1.72 g of 2'-hydroxy-4'-methoxyacetophenone and 6-(4-aminophenyl)-4,5-dihydropyridazin3(2H)one was heated for 16 h at 135° C. The product was crystallized from a mixture of DMA-EtOH. Yield 0.35 g (21%), m.p. 269° C.

EXAMPLE 16

6-[4-(1-(2,4-dihydroxyphenyl)-1-(3,4-dimethoxyphenyl)methylene)-aminophenyl]-4,5-dihydropyridazin-3(2H)one A mixture containing 1.37 g of 2,4-dihydroxy-3',4'-dimethoxybenzophenone and 0.95 g of 6-(4-aminophenyl)-4,5-dihydropyridazin-3(2H)one was heated for 16 h at 160°-170° C. The product was crystallized from ethanol. Yield 0.99 g (44%), m.p. 296°-300° C.

EXAMPLE 17

6-[4-(1-(2,4-dihydroxyphenyl)-3-(3,4-dimethoxyphenyl)propylidene)-aminophenyl]-4,5-dihydropyridazin-3(2H)one A mixture containing 1.0 g of 1-(2,4-dihydroxyphenyl)-3-(3,4-dimethoxyphenyl)propan-1-one and 0.57 g of 6-(4-aminophenyl)-4,5-dihydropyridazin-3(2H)one was heated for 24 h at 160°-170° C. The product was crystallized from ethanol. Yield 0.24 g (10%), m.p. 235°-242° C.

EXAMPLE 18

6-[4-(1-(2,4-dihydroxyphenyl)-2-(3,4-dichlorophenyl)ethylidene)-aminophenyl]-4,5-dihydropyridazin-3(2H)one A mixture containing 0.36 g of 2-(3,4-dichlorophenyl)-1-(2,4-dihydroxyphenyl)ethan-1-one and 6-(4-aminophenyl)-4,5-dihydropyridazin-3(2H)one was heated for 4 h at 150° C. The product was triturated with ethyl acetate. Yield 0.15 g (30%), m.p. 274°-277° C.

EXAMPLE 19

6-[4-(1-(2,4-dihydroxyphenyl)-4-phenyl-butylidene)aminophenyl]-4,5-dihydropyridazin-3(2H)one A mixture containing 0.2 g of 1-(2,4-dihydroxyphenyl)4-phenylbutan-1-one and 6-(4-aminophenyl)-4,5-dihydropyridazin-3(2H)one was heated for 24 h at 150° C. The product was treated with ethyl acetate. Yield 0.2 g (88%), m.p. 274°-280° C.

EXAMPLE 20

6-[4-(1-(2,4-dihydroxyphenyl)-3,3-diphenyl)-propylidene)-aminophenyl]-4,5-dihydropyridazin-3(2H)one A mixture containing 1.0 g of 1-(2,4-dihydroxyphenyl)-3,3-diphenyl-propan-1-one and 0.57 g of 6-(4-aminophenyl)-4,5-dihydropyridazin-3(2H)one was heated for 24 h at 180°-190° C. The product was crystallized from ethanol. Yield 0.04 g (3%),C. The m.p. 295°-300° C.

EXAMPLE 21

4,5-dihydro-5-methyl-6-(2,4-dihydro-2-phenyl-6-quinoxalinyl)pyridazin-3(2H)one

A solution containing 0.3 g of 6-(3,4-diaminophenyl)-5-methyl-4,5-dihydropyridazin-3(2H)one, 0.3 g of phenacyl bromide and 0.14 g of sodium acetate in 2.6 ml of ethanol was stirred for 3.5 h at room temperature. The product was washed with water and ethanol. Yield 0.1 g (23%), m.p. 209°-215° C.

EXAMPLE 22

4,5-dihydro-5-methyl-6-(2-phenyl-6-quinoxalinyl)-pyridazin-3(2H)one

A solution containing 0.1 g of the compound described in Example 21 in 10 ml of ethanol was refluxed for 4.5 h. The product was filtered. Yield 0.05 g (50%), m.p. 243°-245° C.

EXAMPLE 23

6-[4-(1-(2,4-dihydroxyphenyl)ethylidene)aminophenyl]-pyridazin-3(2H)one

A mixture containing 1.8 g of 2',4'-dihydroxyacetophenone and 1.87 g of 6-(4-aminophenyl)pyridazin-3(2H)one was heated for 4 h at 150° C. The product was treated with ethanol. Yield 1.28 g (40%), m.p. 350° C. (decomp).

We claim:

1. A compound of formula I:

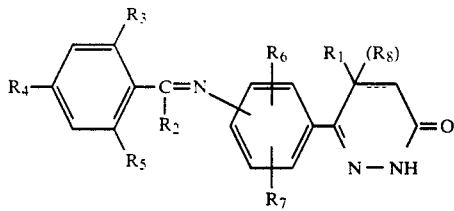

wherein $R_1$ and $R_8$ each independently is a member selected from the group consisting of hydrogen and a lower alkyl group; $R_2$ is selected from the group consisting of hydrogen, lower alkyl, trifluoromethyl, hydroxy $C_{1-18}$ alkyl, halogen $C_{1-18}$ alkyl, $C_{1-18}$ alkoxy $C_{1-18}$ alkyl, $C_{3-6}$ cycloalkyl, phenyl optionally substituted with one to three members selected from the group consisting of halogen, hydroxy, $C_{1-18}$ alkoxy, amino and cyano groups, phenyl $C_{1-3}$ alkyl optionally substituted with one to three members selected from the group consisting of halogen, hydroxy, $C_{1-18}$ alkoxy, amino and cyano groups, phenyl $C_{2-3}$ alkenyl optionally substituted with one to three members selected from the group consisting of halogen, hydroxy, $C_{1-18}$ alkoxy, amino and cyano groups; $R_3$ is selected from the group consisting of hydrogen, lower alkyl, hydroxy $C_{1-18}$ alkyl, halogen, hydroxy, $C_{1-18}$ alkoxy, lower acyloxy, arylcarbonyloxy in which the aryl group is a monocyclic or bicyclic group having from 6 to 10 carbon atoms in the ring portion, formyl, lower acyl, cyano, amino, carboxy and trifluoromethyl groups; $R_4$ and $R_5$ each independently is a member selected from the group consisting of lower alkyl, hydroxy $C_{1-18}$ alkyl, halogen, hydroxy, $C_{1-18}$ alkoxy, lower acyloxy, arylcarbonyloxy in which the aryl group is a monocyclic or bicyclic group having from 6 to 10 carbon atoms in the ring portion, formyl, lower acyl, cyano, amino, carboxy and trifluoromethyl groups; and $R_6$ and $R_7$ each independently is a member selected from the group consisting of hydrogen, amino, lower alkyl, hydroxy, nitro and cyano groups; or a pharmaceutically acceptable salt or a pharmaceutically acceptable ester thereof, with the proviso that said ester is formed only when one or more hydroxy groups are present on one or more of groups $R_2$, $R_3$, $R_4$, $R_5$, $R_6$, and $R_7$.

2. 6-[2,4-Dimethyl-3-((2,4-dihydroxyphenyl)methylene)aminophenyl)]-4,5-dihydropyridazin-3(2H)one.

3. 6-[4-(2,4-Dihydroxyphenyl)methyleneaminophenyl]-4,5-dihydropyridazin-3(2H)one.

4. 6-[4-(1-(2,4-Dihydroxyphenyl)ethylidene)aminophenyl]-4,5-dihydropyridazin-3(2H)one.

5. 6-[4-(2,4-Dihydroxyphenyl)benzylidene)aminophenyl]-4,5-dihydropyridazin-3(2H)one.

6. 6-[4-(1-(2,4-Dihydroxyphenyl)ethylidene)aminophenyl]-4,5-dihydro-5-methylpyridazin-3(2H)one.

7. 6-[4-(1-(2,4-Dihydroxyphenyl)propylidene)aminophenyl]-4,5-dihydropyridazin-3(2H)one.

8. 6-[4-(1-(2,4-Dihydroxyphenyl)ethylidene)aminophenyl]pyridazin-3(2H)one.

9. 6-[4-(1-(2,4-Dihydroxyphenyl)-3-phenylpropylidene)-aminophenyl]-4,5-dihydropyridazin-3(2H)one.

10. 6-[4-(2,4-Dihydroxyphenyl)benzylideneaminophenyl]-5-methyl-4,5-dihydropyridazin-3(2H)one.

11. 6-[4-(1-(2,4-Dihydroxyphenyl)-2-(4-hydroxyphenyl)ethylidene)aminophenyl]-4,5-dihydropyridazin-3(2H)one.

12. 6-[4-(1-(2,4-Dihydroxyphenyl)-1-(3,4-dimethoxyphenyl)-methylene-aminophenyl]-4,5-dihydropyridazin-3(2H)one.

13. 6-[4-(1-(2,4-Dihydroxyphenyl)-3-(3,4-dimethoxyphenyl)propylidene-aminophenyl]-4,5-dihydropyridazin-3(2H)one.

14. 6-[4-(1-(2,4-Dihydroxyphenyl)-2-(3,4-dichlorophenyl)ethylidene-aminophenyl]-4,5-dihydropyridazin-3(2H)one.

15. 6-[4-(1-(2,4-Dihydroxyphenyl)-4-phenylbutylidene)aminophenyl]-4,5-dihydropyridazin-3(2H)one.

16. 6-[4-(1-(2,4-Dihydroxyphenyl)-3,3-diphenyl)propylidene)aminophenyl]-4,5-dihydropyridazin-3(2H)one.

17. A pharmaceutical composition comprising a cardiotonic-, antihypertensive-, or vasodilating-effective amount of a compound, salt or ester thereof as defined in claim 1, together with a pharmaceutically acceptable carrier.

18. A pharmaceutical composition as claimed in claim 17, in unit dosage form.

19. A pharmaceutical composition as claimed in claim 17, or 18, in the form of coated tablets, dragees, capsules, suppositories, emulsions, suspensions or solutions.

20. A composition as claimed in claim 17, further comprising at least one ingredient selected from the group consisting of solvents, gel forming ingredients, dispersion forming ingredients, antioxidants, coloring agents sweeteners and wetting agents.

21. A composition as claimed in claim 18, further comprising at least one ingredient selected from the group consisting of solvents, gel forming ingredients, dispersion forming ingredients, antioxidants, coloring agents, sweeteners and wetting agents.

22. A composition as claimed in claim 19, further comprising at least one ingredient selected from the group consisting of solvents, gel forming ingredients, dispersion forming ingredients, antioxidants, coloring agents, sweeteners and wetting agents.

* * * * *